(12) United States Patent
Basu et al.

(10) Patent No.: US 9,134,258 B2
(45) Date of Patent: Sep. 15, 2015

(54) SYSTEMS AND METHODS FOR IMAGING AND DETECTING SHEET-LIKE MATERIAL

(75) Inventors: Samit Basu, Fremont, CA (US); Todd Jason Gable, Newark, CA (US)

(73) Assignee: Morpho Detection, LLC, Newark, CA (US)

( * ) Notice: Subject to any disclaimer, the term of this patent is extended or adjusted under 35 U.S.C. 154(b) by 455 days.

(21) Appl. No.: 13/542,732

(22) Filed: Jul. 6, 2012

(65) Prior Publication Data

US 2014/0010342 A1    Jan. 9, 2014

(51) Int. Cl.
| | |
|---|---|
| G06K 9/52 | (2006.01) |
| G01N 23/04 | (2006.01) |
| G06T 7/00 | (2006.01) |
| G01N 23/16 | (2006.01) |
| G01N 23/083 | (2006.01) |
| G01V 5/00 | (2006.01) |

(52) U.S. Cl.
CPC ............ *G01N 23/046* (2013.01); *G06T 7/0004* (2013.01); *G01N 23/083* (2013.01); *G01N 23/16* (2013.01); *G01N 2223/419* (2013.01); *G01V 5/005* (2013.01); *G06K 9/52* (2013.01); *G06K 2209/09* (2013.01); *G06T 2207/30112* (2013.01)

(58) Field of Classification Search
CPC .............. G01N 23/04; G01N 21/8851; G01N 2021/8909; G01N 21/86; G01N 21/958; G01N 23/16; G01N 23/18; G01N 2021/8967; G01N 23/046; G01N 2223/419; G06K 9/00; G06K 2209/09; G06K 9/52; G06T 7/0002; G06T 7/004; G06T 2207/30112; G06T 7/0004; G01V 5/005
USPC .......... 378/4, 21, 901; 382/103, 171, 173, 282
See application file for complete search history.

(56) References Cited

U.S. PATENT DOCUMENTS

| | | | |
|---|---|---|---|
| 6,026,143 A * | 2/2000 | Simanovsky et al. | 378/57 |
| 6,345,113 B1 | 2/2002 | Crawford et al. | |
| 7,031,430 B2 | 4/2006 | Kaucic, Jr. et al. | |
| 2005/0036689 A1* | 2/2005 | Mahdavieh | 382/199 |
| 2011/0266440 A1* | 11/2011 | Boughorbel et al. | 250/310 |

* cited by examiner

*Primary Examiner* — Glen Kao
*Assistant Examiner* — Julio M Duarte-Carvajalino
(74) *Attorney, Agent, or Firm* — Armstrong Teasdale LLP

(57) ABSTRACT

A method for imaging an object is provided. The method includes acquiring image data of the object, wherein the image data includes a plurality of original voxels, and identifying, using a processing device, a first subset of voxels from the acquired image data. The method also includes performing a principal component analysis (PCA) on the first subset of voxels and determining whether sheet-like material is present in the object based on the results of the performed PCA on the first subset of voxels.

14 Claims, 4 Drawing Sheets

SYSTEMS AND METHODS FOR IMAGING AND DETECTING SHEET-LIKE MATERIAL

BACKGROUND OF THE INVENTION

The embodiments described herein relate generally to X-ray computed tomography and, more particularly, to imaging and detecting sheet-like material in objects using X-ray computed tomography.

In at least some known computed tomography ("CT") imaging systems, an X-ray source projects a fan-shaped or a cone-shaped beam towards an object to be imaged. The X-ray beam passes through the object, and, after being attenuated by the object, impinges upon an array of radiation detectors. Each radiation detector produces a separate electrical signal that is a measurement of the beam intensity at the detector location. During data acquisition, a gantry that includes the X-ray source and the radiation detectors rotates around the object.

At least some known contraband (e.g., explosives, drugs, weapons, etc.) detection systems utilize CT technology to produce CT images and detect contraband in objects such as luggage, packages, etc. CT volume scanners acquire a plurality of cross-sectional CT slices of an object at regular, closely spaced intervals so that the entire volume of the object is imaged. Each pixel in each CT slice therefore represents a volume, and is referred to as a voxel. The value, or CT number, of each voxel represents an approximation of the density of the material within the voxel. Each voxel represents X-ray attenuation and is related to object density and effective atomic number. Many volume scanners employ multiple rows of detectors arranged in an array, and the object is moved continuously through the gantry while the gantry rotates.

At least some known CT scanners can accurately produce CT numbers for large objects. However, as objects become smaller and/or thinner, the accuracy of the CT number may decrease, as the accuracy of the CT number is limited by the spatial resolution of the scanner and the size of the pixels or voxels. Accordingly, known CT scanners may be unable to image thin objects and as such, may be unable to define a thickness and/or density of objects. Therefore, at least some known CT systems are unable to clearly and accurately image thin objects.

BRIEF SUMMARY OF THE INVENTION

In one aspect, a method for imaging an object is provided. The method includes acquiring image data of the object, wherein the image data includes a plurality of original voxels, and identifying, using a processing device, a first subset of voxels from the acquired image data. The method also includes performing a principal component analysis (PCA) on the first subset of voxels and determining whether sheet-like material is present in the object based on the results of the performed PCA on the first subset of voxels.

In another aspect, an X-ray computed tomography (CT) system for imaging an object is provided. The system includes an X-ray emitter configured to emit X-ray beams that passes through the object, a detector array configured to acquire raw data by detecting the X-ray beams emitted by said X-ray emitter, an image reconstructor configured to generate image data of the object from the image data, the image data including a plurality of original voxels, and a processing device. The processing device is configured to identify a first subset of voxels from the image data, perform a PCA on the first subset of voxels, and determine sheet-like material is present in the object based on the results of the performed PCA on the first subset of voxels.

In yet another aspect, a processing device is provided. The processing device is configured to receive image data of an object, wherein the image data includes a plurality of original voxels, identify a first subset of voxels from the image data, perform a PCA on the first subset of voxels, and determine sheet-like material is present in the object based on the results of the performed PCA on the first subset of voxels.

DETAILED DESCRIPTION OF THE INVENTION

The systems and methods described herein enable imaging and detection of sheet-like material in objects. Original image data of an object, such as a piece of luggage or a package, is acquired. The original image data includes a plurality of original voxels. A first subset of voxels is identified from the acquired image data and then a principal component analysis (PCA) is performed on the first subset of voxels. This PCA enables determination to be made of whether sheet-like material is present in the object. A second subset of voxels is also identified such that the system can determine a thickness and/or density of the sheet-like material in the objects and image such material. An image of the sheet-like material is then displayed. The image may be analyzed and/or displayed to determine whether the imaged object includes any contraband, such as explosives, narcotics, and/or weapons.

Figure 1:
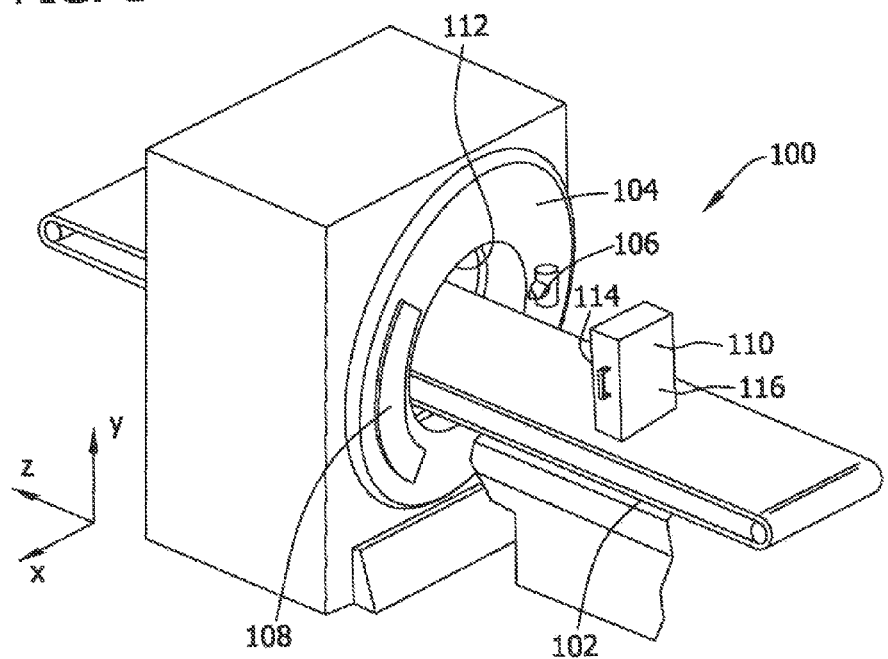
FIG. 1 is a perspective view of an exemplary computed tomography system.

FIG. 1 is a perspective view of a computed tomography (CT) system 100. CT system 100 includes a conveyor 102 and a gantry 104. Gantry 104 includes an emitter 106 (e.g., an X-ray emitter), a detector array 108, and a gantry tunnel 112. In operation, conveyor 102 moves such that when an object 110 is placed on conveyor 102, conveyor 102 moves the item through gantry tunnel 112 and past gantry 104. During operation, a leading face 114 of object 110 enters gantry tunnel 112 first, and a trailing face 116 of object 110 enters gantry tunnel last.

The direction along which object 110 moves through gantry tunnel 112 is referred to herein as the z-direction, the horizontal direction orthogonal to the z-direction is referred to herein as the x-direction, and the vertical direction orthogonal to the x-direction and the z-direction is referred to herein as the y-direction. Object 110 may have any shape and/or dimensions that enable CT system 100 to function as described herein.

To image object 110, X-ray emitter 106 and detector array 108 are rotated with gantry 104 in an x-y imaging plane that is orthogonal to the z-direction. Gantry 104 is rotated around object 110 such that an angle, or view, at which an X-ray beam intersects object 110 constantly changes. As object 110 passes through gantry 104, gantry 104 gathers X-ray intensity data (also referred to herein as raw data) acquired from detectors in detector array 108 for each view. In the exemplary embodiment, the angular difference between adjacent views is approximately 0.25 degrees. Thus, there are approximately 1440 views in a full rotation of gantry 104. Alternatively, the views may be spaced at any interval that enables CT system 100 to function as described herein.

Figure 2:
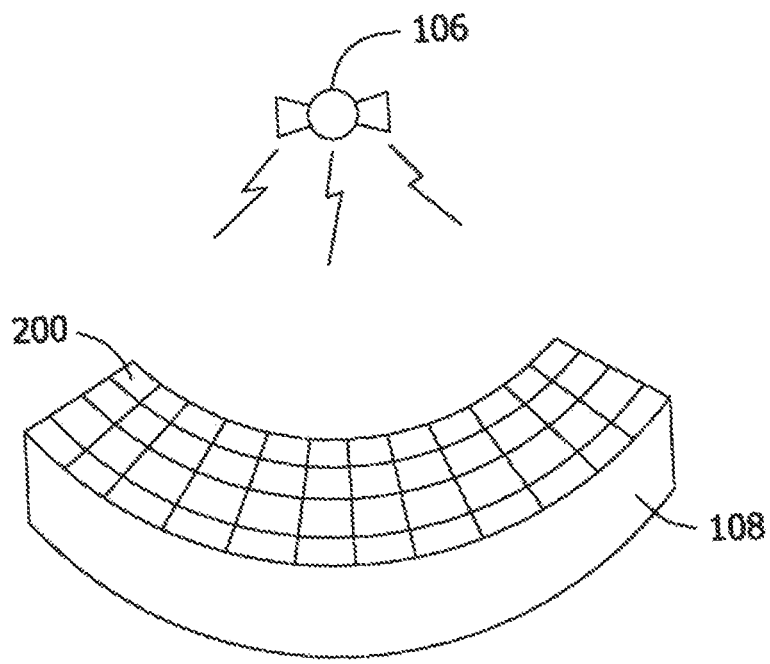
FIG. 2 is a perspective view of an exemplary emitter and detector array that may be used with the computed tomography system shown in FIG. 1.

FIG. 2 is a perspective view of an exemplary emitter 106 and detector array 108 that may be used with CT system 100 (shown in FIG. 1). Emitter 106 emits X-rays that detector array 108 is configured to detect. The operating principles of emitter 106 and detector array 108 will not be discussed in detail herein. Detector array 108 has a plurality of detectors 200. For example, in some embodiments, detector array 108 has thousands of detectors 200. For clarity, a relatively small number of detectors 200 are shown in FIG. 2.

Figure 3:
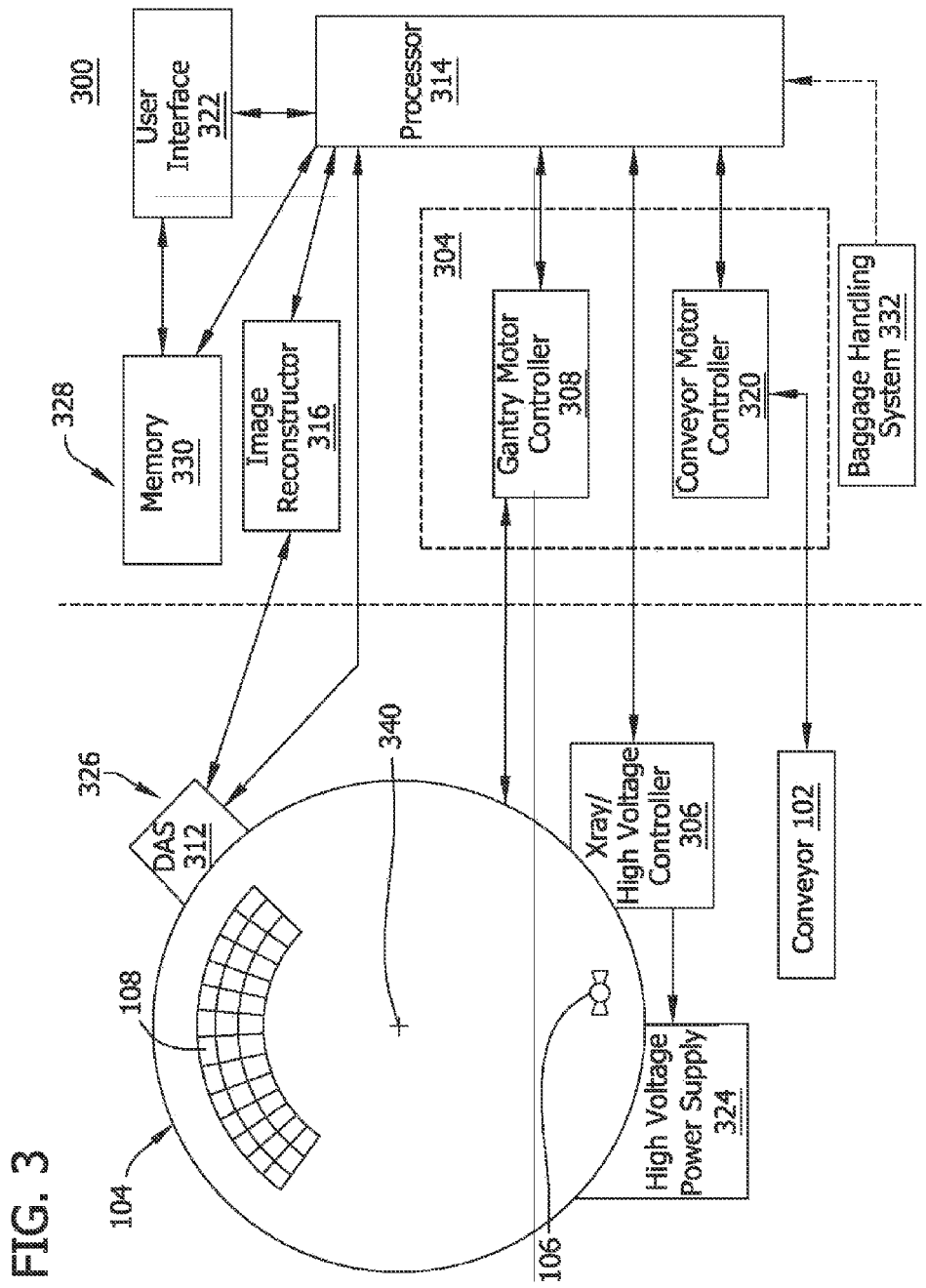
FIG. 3 is a block diagram of an exemplary electronics architecture that may be used with the computed tomography system shown in FIG. 1.

FIG. 3 depicts a block diagram of an electronics architecture 300 that may be used with CT system 100 (shown in FIG. 1). Electronics architecture 300 is separated into moving components 326 and stationary components 328.

Moving components 326 include gantry 104, conveyor 102, an X-ray/high voltage controller 306, a data acquisition system ("DAS") 312, and a high voltage power supply 324. DAS 312, X-ray/high voltage controller 306, and high voltage power supply 324 are secured to (and rotate in unison with) gantry 104 in the exemplary embodiment.

Stationary components 328 include a control mechanism 304, a processor 314, a user interface 322, memory 330, an image reconstructor 316, and a baggage handling system 332. Control mechanism 304 includes a gantry motor controller 308 and a conveyor motor controller 320. Although image reconstructor 316 and processor 314 are shown as separate components in FIG. 3, in some embodiments, image reconstructor 316 may be incorporated as part of processor 314.

Processor 314 may include one or more processing units (e.g., in a multi-core configuration). Further, processor 314 may be implemented using one or more heterogeneous processor systems in which a main processor is present with secondary processors on a single chip. As another illustrative example, processor 314 may be a symmetric multi-processor system containing multiple processors of the same type. Further, processor 314 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

Memory 330 is one or more devices that enable information such as executable instructions and/or other data to be stored and retrieved. Memory 330 may include one or more computer readable media, such as, without limitation, dynamic random access memory (DRAM), static random access memory (SRAM), a solid state disk, and/or a hard disk. Memory 330 may be configured to store, without limitation, application source code, application object code, source code portions of interest, object code portions of interest, configuration data, execution events and/or any other type of data. In some embodiments, executable instructions are stored in memory 330. Processor 314 is programmed to perform one or more operations described herein. For example, processor 314 may be programmed by encoding an operation as one or more executable instructions and by providing the executable instructions in memory 330.

Gantry 104 includes emitter 106 and detector array 108. Each detector 200 (shown in FIG. 2) in detector array 108 produces an electrical signal that represents the intensity of an impinging X-ray beam and hence allows estimation of the attenuation of the beam as it passes through object 110. During a scan to acquire X-ray projection data, gantry 104 and the components mounted thereon rotate about a center of rotation 340. X-ray/high voltage controller 306 provides power to X-ray emitter 106, gantry motor controller 308 controls the rotational speed and position of gantry 104, and conveyor motor controller 320 controls the operation of conveyor 102.

DAS 312 samples analog data from detector array 108 and converts the data to digital signals for subsequent processing. Accordingly, raw data is acquired for object 110 while object 110 passes through gantry tunnel 112. Image reconstructor 316 receives the raw data from DAS 312 and performs high-speed image reconstruction to generate image data from the raw data. In the exemplary embodiment, the image data is generated using filtered back-projection methods. Alternatively, the image data may be generated using any suitable image reconstruction method.

In the exemplary embodiment, the image data is a plurality of voxels that form a three-dimensional image of object 110. Each voxel represents X-ray attenuation and is related to density and effective atomic number. Specifically, each voxel has a CT number that represents an approximate density of the material within the voxel. In the exemplary embodiment, the CT numbers are in Hounsfield units. Processor 314 processes the image data, as described in detail below.

Figure 4:
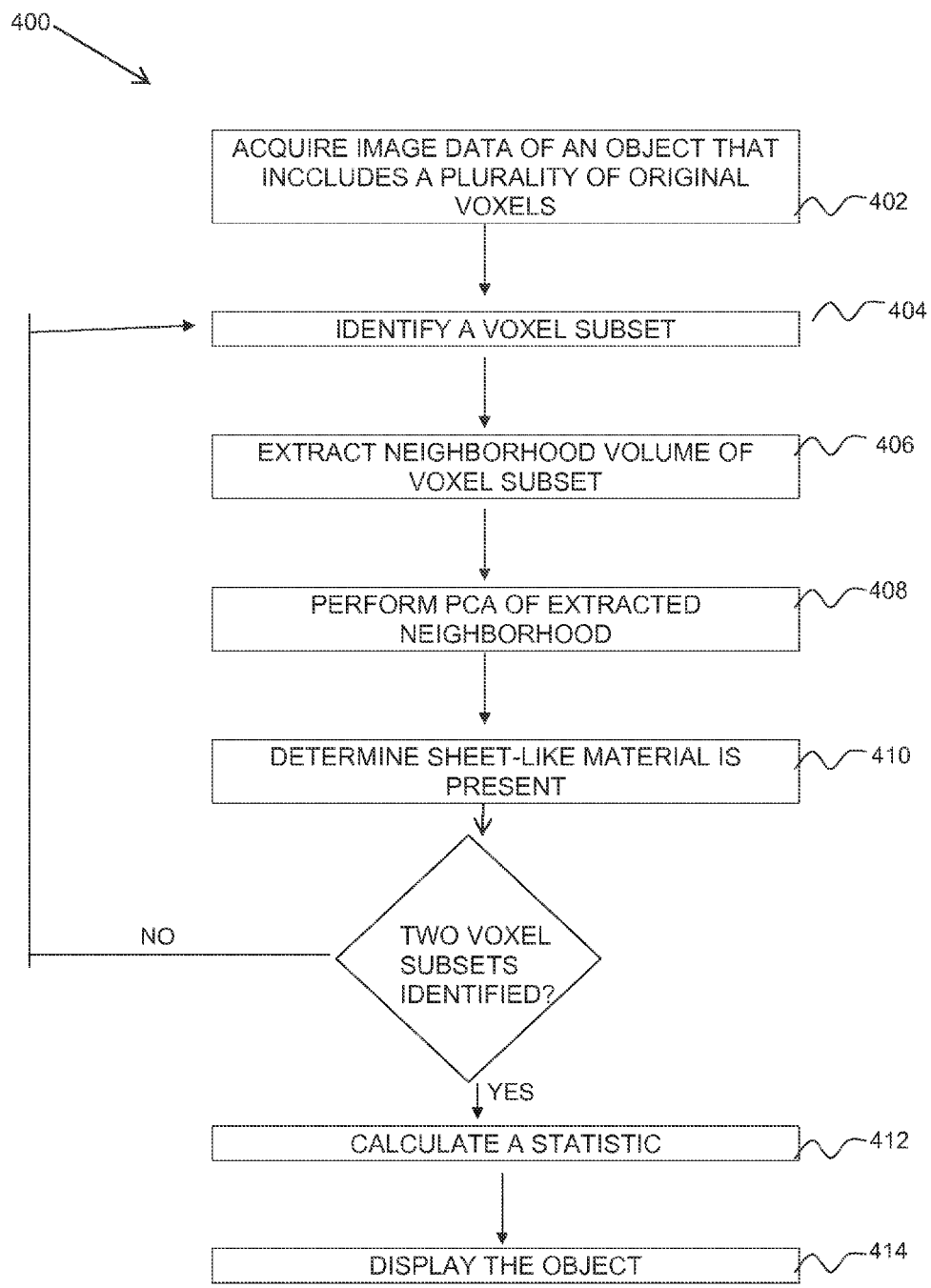
FIG. 4 is a flowchart of an exemplary method for imaging an object that may be used with the computed tomography system shown in FIG. 1.

FIG. 4 is a flowchart of an exemplary method 400 for imaging an object, such as object 110 (shown in FIG. 1). Image data including a plurality of original voxels is acquired 402 for the object, where each original voxel in the image data has an associated original CT number. The image data may be acquired 402 using an X-ray CT system, such as CT system 100 (shown in FIG. 1).

In the exemplary embodiment, a first subset of voxels is identified 404 from the image data. In one embodiment, the first subset is identified 404 by sampling a predetermined ordinal number (e.g. every $N^{th}$ voxel, or every 7th voxel). Alternatively, the first subset can be identified 404 in any manner that facilitates imaging as described herein, including but not limited to, selecting a random subset and selecting all possible voxels.

Once the first subset is identified 404, a neighborhood around each voxel in the first subset is extracted 406 in 3D. In the exemplary embodiment, an N×N×N neighborhood volume is extracted for each voxel. A principal component analysis (PCA) is then performed 408 on each neighborhood extracted 406. In one embodiment, the PCA is performed 408 by computing the covariance matrix of the neighborhood by the equation:

$$E[(x-m)(x-m)'] \qquad (1)$$

In such an equation, "x" represents the position vector and, and "m" represents the mean. In the exemplary embodiment, three eigenvalues result for the extracted 406 neighborhood from the performed PCA 408. The three eigenvalues are compared to each other to determine 410 if sheet-like material is present. In one embodiment, sheet-like material is determined 410 to be present for the voxel when two eigenvalues are relatively large with respect to a third eigenvalues. In the exemplary embodiment, a determination is made as to whether or not the object is sheet-like based on the total number of sheet-like voxels. Voxels determined to be sheet-like are added together to form a sheet-like voxel grouping that is divided by the total number of voxels computed to result in a sheet-like ratio. If the ratio is above a predetermined threshold (e.g, $\frac{2}{3}$ or $\frac{1}{2}$) object 110 is determined 410 to include sheet-like material.

Once an object is determined 410 to include sheet-like material, a thickness and/or density of the material is calculated. In the exemplary embodiment, to calculate a thickness and/or density of the material two voxel subsets are used. Similar to the steps described with the first voxel subset, a second voxel subset is identified 404 from the image data. In one embodiment, the second subset is identified 404 by sampling a predetermined ordinal number (e.g. every Nth voxel, or every 7th voxel). Alternatively, the second subset can be identified 404 in any manner that facilitates imaging as described herein, including but not limited to, selecting a random subset and selecting all possible voxels.

Once the second subset is identified 404, a neighborhood around each voxel in the second subset is extracted 406 in 3D. In the exemplary embodiment, an N×N×N neighborhood volume is extracted for each voxel. PCA is then performed 408 on each neighborhood extracted 406 resulting in three eigenvalues that are compared to each other to determine 410 if sheet-like material is present.

In the exemplary embodiment, the smallest of the three eigenvalues, over both the subsets, is calculated 412 to determine a statistic which represents the thickness and/or density of the material. In one embodiment, statistics that are calculated 412 include, but are not limited to, a mean, a median, and a mode. In one embodiment, the calculated 412 statistic is corrected for the physical pitch of the voxel grid.

Using the image data, an image, and resulting thickness, of the object is displayed 414 on a display device. In the exemplary embodiment, the display device is part of user interface 322 (shown in FIG. 3), and may include, for example, a cathode ray tube (CRT), a liquid crystal display (LCD), an organic LED (OLED) display, and/or an "electronic ink" display. The image data may be analyzed to determine whether the object contains contraband (e.g., explosives, drugs, weapons, etc.). For example, the processing device may perform one or more image analysis operations on the image data and/or an operator may visually inspect the displayed image of the object for contraband.

The embodiments described herein enable imaging and detection of sheet-like material in objects. Original image data of an object, such as a piece of luggage or a package, is acquired. The original image data includes a plurality of original voxels. A first subset of voxels is identified from the acquired image data and then a principal component analysis (PCA) is performed on the first subset of voxels. This PCA enables determination to be made of whether sheet-like material is present in the object. A second subset of voxels is also identified such that the system can determine a thickness and/or density of the sheet-like material in the objects and image such material. An image of the sheet-like material is then displayed. The image may be analyzed and/or displayed to determine whether the imaged object includes any contraband, such as explosives, narcotics, and/or weapons.

A technical effect of the systems and methods described herein includes at least one of: (a) acquiring image data of the object, wherein the image data includes a plurality of original voxels; (b) identifying, using a processing device, a first subset of voxels from the acquired image data; (c) performing a principal component analysis (PCA) on the first subset of voxels; and (d) determining sheet-like material is present in the object based on the results of the performed PCA on the first subset of voxels.

A computer, such as those described herein, includes at least one processor or processing unit and a system memory. The computer typically has at least some form of computer readable media. By way of example and not limitation, computer readable media include computer storage media and communication media. Computer storage media include volatile and nonvolatile, removable and nonremovable media implemented in any method or technology for storage of information such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Combinations of any of the above are also included within the scope of computer readable media.

Exemplary embodiments of methods and systems for imaging an object are described above in detail. The methods and systems are not limited to the specific embodiments described herein, but rather, components of systems and/or steps of the methods may be utilized independently and separately from other components and/or steps described herein. Accordingly, the exemplary embodiment can be implemented and utilized in connection with many other applications not specifically described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for imaging an object, said method comprising:
    acquiring image data of the object, wherein the image data includes a plurality of original voxels;
    identifying, using a processing device, a first subset of voxels and a second subset of voxels from the acquired image data;
    performing a principal component analysis (PCA) on the first subset of voxels to produce a first set of eigenvalues and the second subset of voxels to produce a second set of eigenvalues;
    determining whether sheet-like material is present in the object based on the results of the performed PCA on the first subset of voxels; and
    determining a thickness of the sheet-like material by comparing the results of the performed PCA on the first subset of voxels and the results of the performed PCA on the second subset of voxels, and by comparing the smallest eigenvalue from the first set of eigenvalues to the smallest eigenvalue from the second set of eigenvalues.

2. A method in accordance with claim 1, wherein determining whether sheet-like material is present comprises comparing the first set of eigenvalues to each other.

3. A method in accordance with claim 1, wherein identifying a first subset of voxels comprises identifying a 3-dimensional (3D) volume centered on a voxel of interest.

4. A method in accordance with claim 1, wherein identifying a first subset comprises at least one of selecting a random subset and selecting a subset including a voxel from a predetermined ordinal number.

5. A method in accordance with claim 1, further comprising:
determining a plurality of statistics for the smallest eigenvalue from the first set of eigenvalues and the smallest eigenvalue from the second set of eigenvalues, wherein the plurality of statistics comprise one or more of: a mean, a median, and a mode; and
correcting the plurality of statistics for a physical pitch of the first subset of voxels and for the second subset of voxels.

6. An X-ray computed tomography (CT) system for imaging an object, the system comprising:
an X-ray emitter configured to emit X-ray beams that pass through the object;
a detector array configured to acquire raw data by detecting the X-ray beams emitted by said X-ray emitter;
an image reconstructor configured to generate image data of the object from the raw data, the image data including a plurality of original voxels; and
a processing device configured to:
identify a first subset of voxels and a second subset of voxels from the generated image data;
perform a principal component analysis (PCA) on the first subset of voxels to produce a first set of eigenvalues and the second subset of voxels to produce a second set of eigenvalues;
determine whether sheet-like material is present in the object based on the results of the performed PCA on the first subset of voxels; and
determine a thickness of the sheet-like material by comparing the results of the performed PCA on the first subset of voxels and the results of the performed PCA on the second subset of voxels, and by comparing the smallest eigenvalue from the first set of eigenvalues to the smallest eigenvalue from the second set of eigenvalues.

7. An X-ray CT system in accordance with claim 6, wherein to determine whether sheet-like material is present, said processing device is further configured to compare the first set of eigenvalues to each other.

8. An X-ray CT system in accordance with claim 6, wherein said processing device is further configured to identify a 3-dimensional (3D) volume centered on a voxel of interest.

9. An X-ray CT system in accordance with claim 6, wherein to identify a first subset, said processing device is further configured to identify a first subset by at least one of selecting a random subset and selecting a subset including a voxel from a predetermined ordinal number.

10. An X-ray CT system in accordance with claim 6, wherein said processing device is further configured to:
determine a plurality of statistics for the smallest eigenvalue from the first set of eigenvalues and the smallest eigenvalue from the second set of eigenvalues, wherein the plurality of statistics comprise one or more of: a mean, a median, and a mode; and
correct the plurality of statistics for a physical pitch of the first subset of voxels and for the second subset of voxels.

11. A processing device configured to:
receive image data of an object, wherein the image data includes a plurality of original voxels;
identify a first subset of voxels and a second subset of voxels from the image data;
perform a principal component analysis (PCA) on the first subset of voxels to produce a first set of eigenvalues and the second subset of voxels to produce a second set of eigenvalues;
determine whether sheet-like material is present in the object based on the results of the performed PCA on the first subset of voxels; and
determine a thickness of the sheet-like material by comparing the results of the performed PCA on the first subset of voxels and the results of the performed PCA on the second subset of voxels, and by comparing the smallest eigenvalue from the first set of eigenvalues to the smallest eigenvalue from the second set of eigenvalues.

12. A processing device in accordance with claim 11, wherein to determine whether sheet-like material is present, said processing device is further configured to compare the first set of eigenvalues to each other.

13. A processing device in accordance with claim 11, wherein said processing device is further configured to identify a 3-dimensional (3D) volume centered on a voxel of interest.

14. A processing device in accordance with claim 11, wherein said processing device is further configured to:
determine a plurality of statistics for the smallest eigenvalue from the first set of eigenvalues and the smallest eigenvalue from the second set of eigenvalues, wherein the plurality of statistics comprise one or more of: a mean, a median, and a mode; and
correct the plurality of statistics for a physical pitch of the first subset of voxels and for the second subset of voxels.

* * * * *